United States Patent
Chen et al.

(10) Patent No.: US 7,067,304 B2
(45) Date of Patent: Jun. 27, 2006

(54) *MONASCUS PURPUREUS* MUTANTS AND THEIR USE IN PREPARING FERMENTATION PRODUCTS HAVING BLOOD PRESSURE LOWERING ACTIVITY

(75) Inventors: Yen-Lin Chen, PingChen (TW); Ing-Er Hwang, Koahsiung Hsien (TW); Ming-Chin Lin, HsinChu Hsien (TW); Chien-Cho Chen, HsinChu (TW); Gwo-Fung Yuan, HsinChu (TW)

(73) Assignee: Food Industry Research and Development Institute, Taiwan (CN)

( * ) Notice: Subject to any disclaimer, the term of this patent is extended or adjusted under 35 U.S.C. 154(b) by 116 days.

(21) Appl. No.: 10/629,198

(22) Filed: Jul. 29, 2003

(65) Prior Publication Data

US 2004/0047842 A1   Mar. 11, 2004

(30) Foreign Application Priority Data

Aug. 15, 2002   (TW) ............... 91118398 A

(51) Int. Cl.
*C12N 1/14*   (2006.01)
*C12N 1/16*   (2006.01)
*C12P 7/52*   (2006.01)
*C12P 1/02*   (2006.01)

(52) U.S. Cl. ............... 435/254.1; 435/255.1; 435/141; 435/171; 435/911

(58) Field of Classification Search ............ 435/254.1, 435/255.1, 155.1, 141, 171, 911
See application file for complete search history.

(56) References Cited

U.S. PATENT DOCUMENTS 4,323,648 A * 4/1982 Tanzawa et al. ............ 435/125
5,472,730 A * 12/1995 Saikusa et al. ............. 426/618
6,635,467 B1 * 10/2003 Chen et al. ................. 435/243

FOREIGN PATENT DOCUMENTS

| JP | 61197524 | 9/1986 |
| JP | 62298598 | 12/1987 |
| JP | 7274978 | 10/1995 |
| JP | 2000279163 | 10/2000 |
| WO | 0131048 | 5/2001 |

OTHER PUBLICATIONS

Derwent Japan Abstract JP62298598 Dated Dec. 25, 1987 "New Hypotensive Fraction in Culture Broth of Monascus Sp. Mould-Absorbed on Acidic Cation Exchange Region, Washing and Eluting by Pyridine Acetate Buffer" Copyright 1996-1998 Derwent Information Limited.

Derwent Japan Abstract JP2000279163 Dated Oct. 10, 2000 "Manufacture of High Monascus Content Food Having Hypotensive Effect, Involves Using White Rice, Soya Beans or Wheat as Koji-Producing Raw Material and Hydrolyzing to Obtain Koji at Specified Moisture Content" Derwent World Patents Index Copyright 2001.

Japan Abstract of JP61197524 Dated Sep. 1, 1986 T. Shoichi, et al. "Remedy for Hypertension".

Japan Abstract of JP7274978 Dated Oct. 24, 1995 Endo Akira, et al. "Production of Ang-Khak Colorant".

Yasuhiro Kohama, et al. Chem. Pharm. Bull. 1987; "Isolation and Identification of Hypotensive Principles in Red-Mold Rice" vol. 35 (6) (1987) pp. 2484-2489.

P.J. Blanc, et al. International Journal of Food Microbiology "Characterization of Monascidin A From *Monascus*as Citrinin" vol. 27 (1995) pp. 201-213.

* cited by examiner

*Primary Examiner*—Vera Afremova
(74) *Attorney, Agent, or Firm*—Ladas and Parry LLP

(57) ABSTRACT

The invention relates to *Monascus purpureus* mutants, which are useful in the preparation of fermentation products having blood pressure lowering activity with a very low amount of citrinin.

The invention also provides a process for preparing the fermentation products having blood pressure lowering activity using the *Monascus purpureus* mutants, and the use of the fermentation products in lowering blood pressure.

11 Claims, No Drawings

MONASCUS PURPUREUS MUTANTS AND THEIR USE IN PREPARING FERMENTATION PRODUCTS HAVING BLOOD PRESSURE LOWERING ACTIVITY

FIELD OF THE INVENTION

The invention provides mutants of *Monascus purpureus*; and their use in preparing products having blood pressure lowering activity.

BACKGROUND OF THE INVENTION

In recent years, cardiovascular diseases, such as hypertension, have become one of the major reasons causing death, and the population having these diseases increases every year. Since hypertension is a chronic disease, the patients have to take anti-hypertension drugs for a long period of time. According to the statistical data of Japan, the market of anti-hypertension drugs is steady at 50 billion yen annually, and the market of health food relating to blood pressure control increased from 1.4 billion yen in 1997 to 7.2 billion yen in 1999. Therefore the demand of the drugs and foods having blood pressure lowering activity in the world increases every year.

Historically, the genus *Monascus* has been wildly used in preparing traditional Chinese medicine and food, and used as food additives in China. JP 61197524 discloses that the metabolites from the genuses of *Aspergillus* and *Monascus* can improve the syndrome of hypertension. Kohama et. al. (Chemical and Pharmaceutical Bulletin, 35, (1987), 2484–2489) found that gamma-aminobutyric acid (GABA) and acetylcholine (Ach) in the fermentation liquid have the effect of lowing blood pressure. JP 62298598 discloses a method for collecting the materials having blood pressure lowering activity. JP 03090031 provides an improved culture medium for *Monascus purpureus* in increasing the production of the materials having blood pressure lowering activity. JP 2000279163 discloses a food having blood pressure lowering activity prepared from *Monascus purpureus*, which contains GABA and glucosamine. WO 01/31048 A1 discloses a nitric oxide donor composition prepared by using *Monascus purpureus* to ferment red rice, which has the effects on vasodilation and lowering blood pressure.

Blanc et. al. (International Journal of Food Micorbiology; 27, (1995), 201–213) found that *Monascus purpureus* produces a fungal toxin, named citrinin, which caused considerable attention to the safety of the *Monascus* products. JP 7274978 discloses a mutation method for reducing the amount of citrinin (lower than 1 ppm) in the production of red pigment. However, the activity of lowering blood pressure was not disclosed thereby.

The microorganisms of the genus of *Monascus* have been widely used in producing the material for lowering blood pressure, but the products thereof contain a high amount of citrinin. Therefore, the safety of the fermentation product is of concern.

SUMMARY OF THE INVENTION

The present invention provides novel mutants of *Monascus purpureus*, which produce the fermentation products having blood pressure lowering activity in a solid or liquid medium comprising cheap natural raw materials without any additional processing steps, and the products contain a low amount of citrinin.

The invention also provides a method for producing the fermentation products having blood pressure lowering activity by using the novel mutants of the present invention.

The invention further provides pharmaceutical compositions and food additives prepared by the fermentation products produced by the novel mutants of the present invention.

DETAILED DESCRIPTION OF THE INVENTION

The present invention provides a mutant of *Monascus purpureus* obtained by mutating *Monascus purpureus* and screening therefrom. While the mutant is incubated in the culture medium containing 60 g/l of rice powder, 30 g/l of soybean powder and 5 g/l of $MgSO_4.7H_2O$, and when the amount of GABA in the fermentation product is up to 0.03 mg/ml, the amount of citrinin is less than 1 ppm, preferably less than 0.5 ppm, and most preferably less than 0.15 ppm.

According to the present invention, all known GABA producing strains of *Monascus purpureus* can be used as the parent strain for preparing the mutant; such as *Monascus purpureus* CCRC 31497 (also named as ATCC 16375, CBS 280.34 and IFO 4489), CCRC 31498 (also named as ATCC 16358, CBS 281.34 and IFO 4486), CCRC 31499 (also named as *Monascus anka*, ATCC 16360, CBS 283.34, IFO 4478, and KFCC 11832), CCRC 31501 (also named as ATCC 16362, CBS 285.34 and IFO 4485), CCRC 31504 (also named as ATCC 16367, CBS 288.34 and IFO 4484), CCRC 31541 (also named as ATCC 16379 and IFO 5965), or CCRC 31542 (also named as ATCC 16365, CBS 109.07 and IFO 4153), which are all available from the Food Industry Research and Development Institute (FIRDI) in Hsin-Chu, Taiwan.

According to the present invention, the "mutant" refers to a strain whose genetic composition differs by at least one nucleotide relative to its parent strain, and the mutant nucleotide sequence may change the physiology of the cell. A mutant of the present invention can be produced by a number of methods, including random mutagenesis of the parent strain, e.g., by means of a chemical mutagen, a transposon or irradiation, or using the recombinant nucleic acid technology to substitute, delete, or insert one or more nucleotides of nucleotide sequence of the gene of the parent strain (Sambrook, J. Cold Spring Harbor Press, Plainview N.Y.; Ausubel, R. M. et. al. (1995), Current protocols in Molecular Biology, John Wiley & Sons, New York N.Y.). The mutants, whereby the amount of GABA produced is higher and the citrinin produced is lower than the parent strain, can then be screened and isolated.

According to a preferred embodiment of the present invention, the mutant of *Monascus purpureus* has the properties identical to those of *Monascus purpureus* M022 and M1033. The strains *Monascus purpureus* M022 and M1033 have been deposited with the Food Industry Research and Development Institute, Taiwan, on Feb. 20, 2002, under Accession Nos. CCRC 930052 and CCRC 930053, respectively; and also been deposited with the American Type Culture Collection (ATCC, 10801 University Boulevard, Manassas, Va. 20110-2209, USA) on 21 Jun. 2002 in accordance with the Budapest Treaty, under Accession Nos. PTA-4486 and PTA-4485, respectively.

According to the present invention, the method for producing the fermentation product by using the mutant of *Monascus purpureus* can be performed by fermentation in a solid or liquid cultural medium.

According to the present invention, all known carbon and nitrogen sources can be added to the cultural media. Natural material is the preferable embodiment of the invention, wherein the carbon source includes, but is not limited to rice powder, corn starch, rice starch, wheat starch, glucose, maltose, sucrose, glycerol, and combination thereof; and the nitrogen source includes, but is not limited to soybean powder, soybean albumen, digestive albumen, yeast extract, corn steep liquor, glutamic acid, ammonium chloride, potassium nitrate, and combination thereof.

According to a preferable production method of the present invention, the pH value of the cultural medium is from 3 to 9, and preferably from 5 to 7.

According to the present invention, the fermentation product produced by the mutant contains the substances having blood pressure lowering activity, such as GABA, glucosamine and acetylcholine. GABA is a main substance inhibiting neural transmission in the central nerve system, and the relevant receptors include $GABA_A$ and $GABA_B$. In animal studies, it was found that the activation of $GABA_A$ is associated with the physiological phenomenon of lowering blood pressure, anti-spastic and anti-anxiety activity. If was also proved that GABA has the activity of treating hypertension, and the lowering blood pressure activity of many antihypertension drugs is achieved by means of controlling the amount of GABA. Therefore, the amount of GABA is an important indicator of the blood pressure lowering activity.

According to the present invention, the amount of citrinin in the fermentation product produced by *Monascus purpureus* is less than 1 ppm, preferably less than 0.5 ppm, and most preferably less than 0.15 ppm.

According to the present invention, the fermentation product having blood pressure lowering activity can be directly used as the active component of a pharmaceutical composition or as a food additive. The materials having blood pressure lowering activity in the fermentation product can be further purified by various conventional techniques, for example, the purification and extraction methods disclosed by Kohama et. al. (Chemical and Pharmaceutical Bulletin, 35, (1987), 2484–2489) and in JP 62298598.

The following examples are used for illustrating, but not for limiting the invention.

EXAMPLE 1

General Analysis Method (1) Quantitative Analysis of GABA

A mixture of 0.6 ml of the fermentation liquid of the strain and 0.6 ml of $LaCl_3$ was incubated at 60° C. in a waterbath for 30 min. The mixture was centrifuged, and 0.1 ml of the supernatant was reacted with 50 μl of KOH (1M) in 850 μl of water for 5 min. The reaction product was centrifuged and the supernatant was stored.

The stored supernatant sample (550 μl) was mixed with 150 μl of NADP (4 mM), 200 μl of phosphate buffer solution (pH 8.6) and 50 μl of GABASE (2 units/ml). The absorbance of $OD_{340}$ of the mixed sample was immediately measured with a spectrophotometer and recorded. The mixture was added with 50 μl of α-ketoglutaric acid for reacting for 60 min., the absorbance of $OD_{340}$ was measured again. The difference between the two $OD_{340}$ values measured before and after the reaction was calculated. The difference was compared with the value of a GABA standard to calculate the concentration of GABA in the fermentation liquid sample.

(2) Quantitative Analysis of Citrinin

The following HPLC analysis procedures were used to determine the amount of citrinin in the fermentation liquid of the strain. Seven (7) ml of the fermentation liquid was adjusted to a pH of 3.5 and then incubated for 1 hour. Three (3) ml of ethyl acetate was added into the liquid and after 30 min., the ethyl acetate layer was collected. The steps of addition and collection of ethyl acetate were repeated twice, and then the collected solution was dried.

The dried sample was dissolved in 1 ml of methanol, and then passed through a membrane with a pore size of 0.2 μm. Ten (10) μl of the filtrate was applied for the HPLC analysis under the following conditions:

| | |
|---|---|
| Column: | μBondapak $C_{18}$ (10 μm, Waters, source place) |
| Flow rate: | 1.0 ml per minute |
| Detector: | UV detector (Waters photodiary assay 966, analysis wave 225–345 nm) |
| Mobile phase (gradient): | 0.8% phosphoric acid:acetonenitrile:2-propanol is from 60:35:5 to 25:70:5 |
| Running time: | 20 minutes |
| Retention time: | 11 minutes |

The concentrations of citrinin were calculated by comparing the values of the detected samples with that of the standard (Sigma).

EXAMPLE 2

Mutagenesis and Screening of the Mutants of the Invention

*Monascus purpureus* strain CCRC 31499 was inoculated onto a PDA (infusion from potato 20%, Bacto Dextrose 2% and agar 2%) slant and incubated at 30° C. for 7 days. The spores were washed off with sterile water. The collected spore suspension (containing over $1 \times 10^7$ spores per ml) was irradiated with UV light for 2 min. After a serial dilution, the diluted spore suspension samples were spread on PDA plates and incubated at 30° C. for 2 to 3 days. The colonies were then inoculated into the medium containing rice powder 60 g/l, soybean powder 30 g/l and $MgSO_4.7H_2O$ 5 g/l to test the stability of the mutants and to determine the amounts of GABA and citrinin produced.

A stable mutant was isolated and designated as *Monascus purpureus* M022. The mutant was inoculated onto a PDA slant and incubated at 30° C. for 7 days. The spores were washed off with sterile water. The spore suspension ($5 \times 10^5$ spores) was transferred to a 250 ml flask containing 50 ml of the medium containing rice powder 60 g/l, soybean powder 30 g/l and $MgSO_4.7H_2O$ 5 g/l and incubated at 30° C. with shaking at 150 rpm for 5 to 7 days. The fermentation liquid produced by the mutant was collected and the amounts of GABA and citrinin were determined. The result show that the amounts of GABA and citrinin were 0.039 mg/ml and less than 0.15 ppm, respectively. Under the same conditions, the amounts of GABA and citrinin in the fermentation liquid produced by the parent strain *Monascus purpureus* CCRC 31499 were 0.031 mg/ml and 2.1 ppm, respectively.

By the mutation method described above, *Monascus purpureus* M022 was mutated again and another mutant designated as *Monascus purpureus* M1033 was isolated. In the fermentation liquid produced by the mutant in the medium containing flour 80 g/l, yeast extract 10 g/l and glutamic acid 10 g/l, the amounts of GABA and citrinin were 2.07 mg/l and less than 0.15 ppm, respectively. Under the same conditions, the amounts of GABA and citrinin in the fermentation liquid produced by *Monascus purpureus* M022 were 0.834 mg/l and less than 0.15 ppm, respectively.

The morphologic characteristics of *Monascus purpureus* M022 are shown as follows:

CYA Medium (Containing Sucrose 30 g/l, $NaNO_3$ 3 g/l, $K_2HPO_4$ 1.0 g/l, $MgSO_4$ 0.5 g/l, KCl 0.5 g/l, $FeSO_4$ 0.01 g/l, Yeast Extract 1 g/l and Agar 15 g/l)

After being cultivated for 7 days, the colonies showed a yellowish orange color and had a diameter from 1 to 14 mm, and the color of the aerial mycelium was white.

After being cultivated for 10 days, the colonies showed a yellowish orange color and had a diameter from 30 to 32 mm, and the color of the aerial mycelium was white.

The conidiophore stalk was colorless and had irregular branches.

The conidiospores were in the shape of a smooth pear. The diameter of each conidiospore was 3–4×9.5–12.5 μm and the thickness of the wall was 2 μm.

After being cultivated in CYA medium for 21 days, no ascocarp was found.

MEA Medium (Containing Maltose Extract 20 g/l, Peptone 1 g/l, Glucose 20 g/l, and Agar 15 g/l)

After being cultivated for 7 days, the colonies showed a reddish orange color and had a diameter from 28 to 30 mm.

After being cultivated for 10 days, the colonies showed a reddish orange color and had a diameter from 34 to 37 mm.

The conidiophore stalk was red with irregular branches.

After being cultivated in MEA medium for 21 days, the ascocarps were not fully mature and the ascospores were oval-shaped (4.5–5×5–6 μm).

The morphologic characteristics of the *Monascus purpureus* M1033 are shown as follows:

CYA Medium (Containing Sucrose 30 g/l, $NaNO_3$ 3 g/l, $K_2HPO_4$ 1.0 g/l, $MgSO_4$ 0.5 g/l, KCl 0.5 g/l, $FeSO_4$ 0.01 g/l, Yeast Extract 1 g/l and Agar 15 g/l)

After being cultivated for 7 days, the colonies showed a yellowish orange color and had a diameter from 13 to 14 mm and the aerial mycelium was short, small and very little was found.

After being cultivated for 10 days, the colonies showed a yellowish orange color and had a diameter from 17 to 18 mm, and the aerial mycelium was short, small and very little was found.

The conidiophore stalk was colorless had "Z" shaped irregular branches and the wall was smooth.

The conidiospores were in the shape of a pear or ellipse and had a diameter of 6–12×8.5–13 μm.

The diameter of the ascocarps was from 30 to 35 μm. The ascospores were in the shape of an oval with a diameter of 4.5–5×5.5–6 μm.

MEA Medium (Containing Maltose Extract 20 g/l, Peptone 1 g/l, Glucose 20 g/l, and Agar 15 g/l)

After being cultivated for 7 days, the colonies showed a reddish orange color with a diameter from 29 to 30 mm, and the aerial mycelium was short, small and very little was found.

After being cultivated for 10 days, the colonies showed a reddish orange color with a diameter from 41 to 42 mm, and the aerial mycelium was short, small and very little was found.

The conidiophore stalk was colorless and had irregular branches.

After being cultivated in MEA medium for 21 days, the ascocarps were not fully mature.

The comparison between *Monasus purpureus* mutant strains M022, M1033 and the parent strain CCRC 31499 is shown in Table 1.

TABLE 1

|  | Parent strain CCRC 31499 | Mutant strain M022 | Mutant strain M1033 |
| --- | --- | --- | --- |
| Size of conidiospore[a] | 8–12 × 10–13 mm | 3–4 × 9.5–12.46 mm | 6–12 × 8.5–13 mm |
| Size of ascocarp[a] | 37–45 mm | None | 30–35 mm |
| Size of ascospore[a] | 4–5 × 5–6 mm | None | 4–5 × 5.5–6 mm |
| GABA (mg/ml) | 0.031[b] | 0.039[b], 0.834[c] | 2.07[c] |
| Citrinin (ppm) | 2.1[b] | <0.15[b], <0.15[c] | <0.15[c] |

[a]cultivated in CYA medium.
[b]cultivated in the cultural medium containing rice powder 60 g/l, soybean powder 30 g/l and $MgSO_4.7H_2O$ 5 g/l.
[c]cultivated in the cultural medium containing flour 80 g/l, yeast extract 10 g/l and glutamic acid 10 g/l.

EXAMPLE 3

The pH Value for the Production of GABA

According to the method described in EXAMPLE 2, the amounts of GABA and citrinin of the fermentation liquid samples of the mutant strains cultivated in the medium containing rice powder 80 g/l, yeast extract 10 g/l and glutamic acid 10 g/l under different pH values were analyzed. The results were shown in Table 2, demonstrating that the mutant strains *Monascus purpureus* M022 and M1033 cultivated under different pH conditions were able to produce a large amount of GABA with a very low amount of citrinin (<0.15 ppm).

TABLE 2

|  | pH value after sterilization | Mutant strain M022[a] | Mutant strain M1033[a] |
| --- | --- | --- | --- |
| pH 3.0 | 3.3 | 0.068 | — |
| pH 4.0 | 4.5 | 0.377 | 0.568 |
| pH 4.5 |  | — | 1.512 |
| pH 5.0 | 5.4 | 0.465 | 2.141 |
| pH 5.5 |  | — | 2.572 |
| pH 6.0 | 5.8 | 0.867 | 2.728 |
| pH 6.5 | 18.93 | — | 2.736 |
| pH 7.0 | 6.3 | 0.821 | 2.688 |
| pH 8.0 | 6.9 | 0.583 | — |
| pH 9.0 | 7.3 | 0.314 | — |

"—" Sample not analyzed
[a]The unit of GABA is mg/ml.
*The amount of citrinin in all samples were lower than the detectable value of 0.15 ppm.

What is claimed is:

1. An isolated mutant, which is *Monascus purpureus* M022 deposited with the American Type Culture Collection under Accession No. PTA-4486.

2. An isolated mutant, which is *Monascus purpureus* M01033 deposited with the American Type Culture Collection under Accession No. PTA-4485.

3. A method for producing a fermentation product, comprising providing the isolated mutant of claim 1 or 2, and cultivating the mutant under fermentation conditions to obtain a fermentation product wherein the fermentation product contains GABA and the amount of citrinin contained therein is less than 1.0 ppm.

4. The method according to claim 3, wherein said fermentation product has blood pressure lowering activity.

5. The method according to claim 3, wherein said mutant is cultivated in a solid or liquid medium.

6. The method according to claim 5, wherein the pH value of said medium is between 3 to 9.

7. The method according to claim 6, wherein the pH value of said medium is between 5 to 7.

8. The method according to claim 3, wherein the amount of citrinin in said fermentation product is lower than 0.5 ppm.

9. The method according to claim 8, wherein the amount of citrinin in said fermentation product is lower than 0.15 ppm.

10. The method according to claim 4, wherein said fermentation product is incorporated as an active ingredient into a pharmaceutical composition or a food additive.

11. The method according to claim 4, which further comprises a purification step of purifying the ingredients having blood pressure lowing activity to obtain the purified ingredients.

* * * * *